US006956021B1

(12) United States Patent
Edwards et al.

(10) Patent No.: US 6,956,021 B1
(45) Date of Patent: Oct. 18, 2005

(54) STABLE SPRAY-DRIED PROTEIN FORMULATIONS

(75) Inventors: David A. Edwards, Boston, MA (US); Jeffrey S. Hrkach, Cambridge, MA (US)

(73) Assignee: Advanced Inhalation Research, Inc., Cambridge, MA (US)

( * ) Notice: Subject to any disclaimer, the term of this patent is extended or adjusted under 35 U.S.C. 154(b) by 0 days.

(21) Appl. No.: 09/383,054

(22) Filed: Aug. 25, 1999

Related U.S. Application Data

(60) Provisional application No. 60/097,796, filed on Aug. 25, 1998.

(51) Int. Cl.[7] .......................... A61K 38/00; A61K 9/14; A61K 38/27; A61K 47/00
(52) U.S. Cl. .......................... 514/2; 424/489; 424/499; 514/951; 514/970; 514/975
(58) Field of Search .............................. 424/489, 499, 424/450; 514/2, 3, 951, 970, 975

(56) References Cited

U.S. PATENT DOCUMENTS

| | | |
|---|---|---|
| 2,470,296 A | 5/1949 | Fields |
| 2,533,065 A | 12/1950 | Taplin et al. |
| 2,992,645 A | 7/1961 | Fowler |
| 3,781,230 A | 12/1973 | Vassiliades et al. |
| 3,957,965 A | 5/1976 | Harley et al. |
| 4,009,280 A | 2/1977 | Macarthur et al. |
| 4,089,800 A | 5/1978 | Temple |
| 4,161,516 A | 7/1979 | Bell |
| 4,173,488 A | 11/1979 | Vassiliades et al. |
| 4,272,398 A | 6/1981 | Jaffe |
| 4,352,883 A | 10/1982 | Lim |
| 4,391,909 A | 7/1983 | Lim |
| 4,466,442 A | 8/1984 | Hilmann et al. |
| 4,480,041 A | 10/1984 | Myles et al. |
| 4,524,769 A | 6/1985 | Wetterlin |
| 4,572,203 A | 2/1986 | Feinstein |
| 4,590,206 A | 5/1986 | Forrester et al. |
| 4,615,697 A | 10/1986 | Robinson |
| 4,679,555 A | 7/1987 | Sackner |
| 4,741,872 A | 5/1988 | De Luca et al. |
| 4,743,545 A | 5/1988 | Torobin |
| 4,774,958 A | 10/1988 | Feinstein |
| 4,789,550 A | 12/1988 | Hommel et al. |
| 4,818,542 A | 4/1989 | De Luca et al. |
| 4,847,091 A | 7/1989 | Illum |
| 4,855,144 A | 8/1989 | Leong et al. |
| 4,857,311 A | 8/1989 | Domb et al. |
| 4,861,627 A | 8/1989 | Mathiowitz et al. |
| 4,865,789 A | 9/1989 | Castro et al. |
| 4,904,479 A | 2/1990 | Illum |
| 4,917,119 A | 4/1990 | Potter et al. |
| 4,963,297 A | 10/1990 | Madden |
| 4,976,968 A | 12/1990 | Steiner |
| 4,994,281 A | 2/1991 | Muranishi et al. |
| 5,033,463 A | 7/1991 | Cocozza |
| 5,064,650 A | 11/1991 | Lew |
| 5,069,936 A | 12/1991 | Yen |
| 5,075,109 A | 12/1991 | Tice et al. |
| 5,100,669 A | 3/1992 | Hyon et al. |
| 5,123,414 A | 6/1992 | Unger |
| 5,145,684 A | 9/1992 | Liversidge et al. |
| 5,160,745 A | 11/1992 | De Luca et al. |
| 5,169,871 A | 12/1992 | Hughes et al. |
| 5,174,988 A | 12/1992 | Mautone et al. |
| 5,195,520 A | 3/1993 | Schlief et al. |
| 5,204,108 A | 4/1993 | Illum |
| 5,204,113 A | 4/1993 | Hartley et al. |
| 5,260,306 A | 11/1993 | Boardman et al. |
| 5,271,961 A | 12/1993 | Mathiowitz et al. |
| 5,306,483 A | 4/1994 | Mautone |
| 5,327,883 A | 7/1994 | Williams et al. |
| 5,334,381 A | 8/1994 | Unger |
| 5,340,587 A | 8/1994 | Milhalko et al. |
| 5,352,435 A | 10/1994 | Unger |
| 5,384,133 A | 1/1995 | Boyes et al. |
| 5,393,524 A | 2/1995 | Quay |
| 5,407,609 A | 4/1995 | Tice et al. |
| 5,456,917 A | 10/1995 | Wise et al. |
| 5,466,841 A | 11/1995 | Horrobin et al. |
| 5,482,946 A | 1/1996 | Clark et al. |
| 5,518,709 A | 5/1996 | Sutton et al. |
| 5,518,998 A | 5/1996 | Bäckström et al. |
| 5,551,489 A | 9/1996 | Trofast et al. |
| 5,580,575 A | 12/1996 | Unger et al. |

(Continued)

FOREIGN PATENT DOCUMENTS

CA     2085884     12/1991

(Continued)

OTHER PUBLICATIONS

Remington's Pharmaceutical Sciences (17th Ed. 1985), pp. 593,604,607,608.*
Maa, Y., et al., "Spray-Drying of Air-Liquid Interface Sensitive Recombinant Human Growth Hormone," *Journal of Pharmaceutical Sciences* vol. 87(2):152-159 (1998).

(Continued)

*Primary Examiner*—S. Mark Clardy
*Assistant Examiner*—Frank Choi
(74) *Attorney, Agent, or Firm*—Elmore, Craig & Vanstone, P.C.; Carolyn S. Elmore; Anne I. Craig

(57) ABSTRACT

Spray-dried particles having improved protein stability are produced by spray-drying a mixture including a protein, a phospholipid and an organic-aqueous co-solvent. Spray-dried particles which include at least 1 weight % phospholipid, having a tap density of less than 0.4 g/cm$^3$ can be prepared. The particles can be delivered to the pulmonary system of a patient.

40 Claims, No Drawings

U.S. PATENT DOCUMENTS

| | | | |
|---|---|---|---|
| 5,607,695 A | 3/1997 | Ek et al. | |
| 5,607,915 A | 3/1997 | Patton | |
| 5,612,053 A | 3/1997 | Baichwal et al. | |
| 5,614,216 A | 3/1997 | Janoff | |
| 5,654,007 A | 8/1997 | Johnson | |
| 5,690,954 A | 11/1997 | Illum | |
| 5,698,721 A | 12/1997 | Heath | |
| 5,707,644 A | 1/1998 | Illum | |
| 5,709,884 A | 1/1998 | Trofast et al. | |
| 5,780,014 A | 7/1998 | Eljamal | |
| 5,795,594 A | 8/1998 | York et al. | |
| 5,804,212 A | 9/1998 | Illum | |
| 5,814,607 A | 9/1998 | Patton | |
| 5,830,853 A | 11/1998 | Bäckström et al. | |
| 5,851,453 A | 12/1998 | Hanna et al. | |
| 5,874,063 A | 2/1999 | Briggner et al. | |
| 5,885,613 A | 3/1999 | Holland et al. | |
| 5,902,802 A | 5/1999 | Heath | |
| 5,922,354 A | 7/1999 | Johnson | |
| 5,928,469 A | 7/1999 | Franks et al. | |
| 5,976,574 A | 11/1999 | Gordon | 424/489 |
| 5,985,248 A | 11/1999 | Gordon et al. | 424/46 |
| 5,985,309 A * | 11/1999 | Edwards et al. | 424/426 |
| 5,993,783 A | 11/1999 | Eljamal | |
| 6,001,336 A | 12/1999 | Gordon | 424/46 |
| 6,019,968 A | 2/2000 | Platz | |
| 6,051,256 A | 4/2000 | Platz | |
| 6,063,138 A | 5/2000 | Hanna et al. | |
| 6,077,543 A | 6/2000 | Gordon et al. | 424/489 |
| 6,080,721 A | 6/2000 | Patton | |
| 6,103,270 A | 8/2000 | Johnson | |
| 6,123,936 A | 9/2000 | Platz | |
| 6,136,295 A | 10/2000 | Edwards et al. | 424/45 |
| 6,136,346 A | 10/2000 | Eljamal | |
| 6,153,224 A | 11/2000 | Staniforth | |
| RE37,053 E | 2/2001 | Hanes et al. | 424/489 |
| 6,187,330 B1 | 2/2001 | Wang et al. | |
| 6,187,344 B1 | 2/2001 | Eljamal | |
| 6,231,851 B1 | 5/2001 | Platz | |
| 6,254,854 B1 | 7/2001 | Edwards et al. | 424/46 |
| 6,258,341 B1 | 7/2001 | Foster | |
| 6,303,582 B1 | 10/2001 | Eljamal | |
| 6,309,671 B1 | 10/2001 | Foster | |
| 6,315,983 B1 | 11/2001 | Eistetter | |
| 6,358,530 B1 | 3/2002 | Eljamal | |
| 6,426,210 B1 | 7/2002 | Franks et al. | |
| 6,433,040 B1 | 8/2002 | Dellamary et al. | |
| 6,632,456 B1 * | 10/2003 | Backstrom et al. | 424/489 |
| 2002/0052310 A1 | 5/2002 | Edwards et al. | |

FOREIGN PATENT DOCUMENTS

| | | |
|---|---|---|
| CA | 1300009 | 5/1992 |
| CA | 1302258 | 6/1992 |
| CA | 2166108 | 1/1995 |
| CA | 2170394 | 3/1995 |
| CA | 2244767 | 1/1997 |
| CA | 2111002 | 8/2000 |
| CA | 2058428 | 9/2000 |
| CA | 2126244 | 9/2000 |
| EP | 0 257 915 A1 | 3/1988 |
| EP | 0 317 120 A1 | 5/1989 |
| EP | 0 324 938 A1 | 7/1989 |
| EP | 0 335 133 A2 | 10/1989 |
| EP | 0 458 745 A1 | 5/1991 |
| EP | 0 213 303 B1 | 9/1991 |
| EP | 0 257 956 B1 | 5/1992 |
| EP | 0 510 731 A1 | 10/1992 |
| EP | 0 634 166 A1 | 1/1995 |
| EP | 0 655 237 A1 | 5/1995 |
| EP | 0 656 206 A1 | 6/1995 |
| EP | 0 072 046 A1 | 2/2003 |
| GB | 1 288 583 | 11/1969 |
| WO | WO 80/02365 | 11/1980 |
| WO | WO 86/06959 | 12/1986 |
| WO | WO 88/04556 | 6/1988 |
| WO | WO 88/09163 | 12/1988 |
| WO | WO 91/04732 | 4/1991 |
| WO | WO 91/06286 | 5/1991 |
| WO | WO 91/06287 | 5/1991 |
| WO | WO 91/12823 | 9/1991 |
| WO | WO 91/16882 | 11/1991 |
| WO | WO 92/18164 | 10/1992 |
| WO | WO 92/21382 | 12/1992 |
| WO | WO 93/25221 | 12/1993 |
| WO | WO 94/04133 | 3/1994 |
| WO | WO 94/07514 | 4/1994 |
| WO | WO 94/08627 | 4/1994 |
| WO | WO 94/16739 | 8/1994 |
| WO | WO 95/00127 | 1/1995 |
| WO | WO 95/07072 | 3/1995 |
| WO | WO 95/24183 | 9/1995 |
| WO | WO 95/31479 | 11/1995 |
| WO | WO 95/35097 | 12/1995 |
| WO | WO 96/09814 | 4/1996 |
| WO | WO 96/15814 | 5/1996 |
| WO | WO 96/23485 | 8/1996 |
| WO | WO 96/32096 | 10/1996 |
| WO | WO 96/32116 | 10/1996 |
| WO | WO 96/32149 | 10/1996 |
| WO | WO 96/40963 | 12/1996 |
| WO | WO 96/41873 | 12/1996 |
| WO | WO 97/03649 | 2/1997 |
| WO | WO 97/26863 | 7/1997 |
| WO | WO 97/36574 | 10/1997 |
| WO | WO 97/41833 | 11/1997 |
| WO | WO 97/44012 | 11/1997 |
| WO | WO 98/16205 | 4/1998 |
| WO | WO 98/29096 | 7/1998 |
| WO | WO 98/29098 | 7/1998 |
| WO | WO 98/29140 | 7/1998 |
| WO | WO 98/29141 | 7/1998 |
| WO | WO 98/31346 | 7/1998 |
| WO | WO 98/51278 | 11/1998 |
| WO | WO 99/16419 | 4/1999 |
| WO | WO 99/16420 | 4/1999 |
| WO | WO 99/16421 | 4/1999 |
| WO | WO 99/16422 | 4/1999 |
| WO | WO 99/66903 | 12/1999 |
| WO | WO 02/09669 A3 | 2/2000 |
| WO | WO 00/15262 | 3/2000 |
| WO | WO 00/21594 | 4/2000 |
| WO | WO 00/33811 | 6/2000 |
| WO | WO 01/00312 A1 | 1/2001 |
| WO | WO 01/13891 A3 | 3/2001 |
| WO | WO 01/32144 A1 | 5/2001 |
| WO | WO 02/11695 A3 | 2/2002 |
| WO | WO 02/054868 A2 | 7/2002 |
| WO | WO 02/055101 A2 | 7/2002 |
| WO | WO 02/087542 A1 | 11/2002 |

OTHER PUBLICATIONS

Mumenthaler, M., et al., "Feasibility Study on Spray-Drying Protein Pharmaceuticals: Recombinant Human Growth Hormone and Tissue-Type Plasminogen Activator," *Pharmaceutical Research*, vol. 11(1):12-20 (1994).

Broadhead, J., et al., "The Effect of Process and Formulation Variables on the Properties of Spray-dried β-Galactosidase," *J. Pharm. Pharmacol.* 46:458-467 (1994).

Patton, J. and Platz, R., "(D) Routes of Delivery: Case Studies (2) Pulmonary Delivery of Peptides and Proteins for Systemic Action," *Advanced Drug Delivery Reviews*, 8:179-196 (1992).

Niven, R., "Delivery of Biotherapeutics by Inhalation Aerosol," *Critical Reviews in Therapeutic Drug Carrier Systems,* 12(2&3):151-231 (1995).

Broadhead, J., et al., "The Spray Drying of Pharmaceuticals," *Drug Development and Industrial Pharmacy,* 18(11&12):1169-1206 (1992).

Adjei, A., and Garren, J., "Pulmonary Delivery of Peptide Drugs: Effect of Particle Size on Bioavailability of Leuprolide Acetate in Healthy Male Volunteers," *Pharm. Res.,* 7(6):565-569 (1990).

Allen, T.M., et al., "Subcutaneous Administration of Liposomes: A Comparison with the Intravenous and Intraperitoneal Routes of Injection," *Biochem. et Biophys. Acta.* 1150:9-16 (1993).

Altshuler, B., et al., "Aerosol Deposition in the Human Respiratory Tract," *Am. Med. Assoc. Arch. of Indust. Health* 15:293-303 (1957).

Anderson, P.J., et al., "Effect of Cystic Fibrosis on Inhaled Aerosol Boluses," *Am. Rev. Respir. Dis.,* 140:1317-1324 (1989).

Anderson, M., et al., "Human Deposition and Clearance of 6-$\mu$m Particles Inhaled with an Extremely Low Flow Rate," *Exp. Lung Res.,* 21:187-195 (1995).

Barrera, D.A., et al., "Synthesis and RGD Peptide Modification of a New Biodegradable Copolymer: Poly(lactic acid-co-lysine)," *J. Am. Chem. Soc.,* 115:11010-11011 (1993).

Beck, L.R., et al., "A New Long-Acting Injectable Microcapsule System for the Administration of Progesterone," *Fertility and Sterility,* 31(5):545-551 (1979).

Benita, S., et al., "Characterization of Drug-loaded Poly(d, l-lactide) Microspheres," *J. of Pharm. Sci* 73(12):1721-1724 (1984).

Blackett, P.M., and G. Buckton, "A Microcalorimetric Investigation of the Interaction of Surfactants with Crystalline and Partially Crystalline Salbutamol Sulphate in a Model Inhalation Aerosol System," *Pharmaceutical Research,* 12(11):1689-1693 (1995).

Brain, J.D., "Physiology and Pathophysiology of Pulmonary Macrophages". In *The Reticuloendothelial System,* Reichard and Filkins, eds. (Plenum Press, New York), pp. 315-327 (1985).

Brown, A.R., et al., "Propellant-Driven Aerosols of Functional Proteins as Potential Therapeutic Agents in the Respiratory Tract," *Immunopharmacology,* 28:241-257 (1994).

Byron, P.R., "Determinants of Drug and Polypeptide Bioavailability from Aerosols Delivered to the Lung," *Adv. Drug. Del. Rev.,* 5:107-132 (1990).

Carroll, B.A., et al., "Gelatin Encapsulated Nitrogen Microbubbles as Ultrasonic Contrast Agents," *Investigative Radiology,* 15:260-266 (1980).

Carroll, B.A., et al., "Ultrasonic Contrast Enhancement of Tissue by Encapsulated Microbubbles," *Radiology,* 143: 747-750 (1982).

Ch'ng, H.S., et al., "Bioadhesive Polymers as Platforms for Oral Controlled Drug Delivery II: Synthesis and Evaluation of Some Swelling, Water-Insoluble Bioadhesive Polymers," *J. of Pharm Sci.,* 74(4):399-405 (1985).

Clark, A., and P. Byron, "Dependence of Pulmonary Absorption Kinetics on Aerosol Particle Size," *Z. Erkrank. Atm. org.,* 166:13-24 (1986).

Clark, A.R., and M. Egan, "Modeling the Deposition of Inhaled Powdered Drug Aerosols," *J. Aerosol Sci.,* 25(1): 175-186 (1994).

Clay, M.M., et al. "Effect of Aerosol Particle Size on Bronchodilatation with Nebulised Terbutaline in Asthmatic Subjects," *Thorax* 41:364-368(1986).

Cohen, S., et al., "Controlled Delivery Systems for Proteins Based on Poly(Lactic/Glycolic Acid) Microspheres," *Pharm. Res.* 8(6):713-720(1991).

Colthorpe, P., et al., "The Pharmacokinetics of Pulmonary-Delivered Insulin: A Comparison of Intratracheal and Aerosol Administration to the Rabbit," *Pharm. Res.* 9(6): 764-768 (1992).

Daly, W.H., et al., "The Preparation of N-Carboxyanhydrides of $\alpha$-Amino Acids Using Bis (Trichloromethyl) Carbonate," *Tetrahedron Lett.,* 29(46): 5859-5862 (1988).

Damms, B. and W. Bains, "The Cost of Delivering Drugs without Needles," *J. Controlled Release,* 8-11 (1996).

Darquenne, C., and M. Paiva, "Two and Three-Dimensional Simulations of Aerosol Transport and Deposition in Alveolar Zone of Human Lung," *Journal of Applied Physiology,* 80(4):1401-1414 (1996).

Davies, C.N., et al., "Breathing of Half-micron Aerosols. I. Experimental.," *J. of Appl. Physiol.* 32(5):591-600(1972).

Davis, S.S., and L. Illum, "Polymeric Microspheres as Drug Carriers," *Biomaterials,* 9:111-115 (1988).

Davis, S.S., et al., "Microspheres as Controlled-Release Systems for Parenteral and Nasal Administration," *Controlled Release Technology,* Chapter 15, pp. 201-213 (1987).

Dorries, A.M., and Valberg P.A., "Heterogeneity of Phagocytosis for Inhaled Versus Instilled Material," *Am. Rev. Respir. Dis.,* 146:831-837 (1992).

Eldridge, J. H., et al., "Biodegradable Microspheres as a Vaccine Delivery System," *Mol. Immunol.,* 28(3):287-294 (1991).

Feinstein, S.B., et al., "Two-Dimensional Contrast Echocardiography I. In Vitro Development and Quantitative Analysis of Echo Contrast Agents," *JACC* 3(1):14-20 (1984).

Ferin, J., et al., "Pulmonary Retention of Ultrafine and Fine Particles in Rats," *Am. J. Respir. Cell Mol. Biol.* 6:535-542 (1992).

Findeisen, W. "Uber Das Absetzen Kleiner, in Der Luft Suspendierter Teilchen in Der Menshlichen Lunge Bei Der Atmung," *Pflugers Arch. D. Ges. Physiol.* 236:367-379 (1935).

Ganderton, D., "The Generation of Respirable Clouds Form Coarse Powder Aggregates," *J. Biopharmaceutical Sciences,* 3(1/2):101-105 (1992).

Gehr, P. et al., "Surfactant and Inhaled Particles in the Conducting Airways: Structural, Stereological, and Biophysical Aspects," *Microscopy Res. And Tech.,* 26:423-436 (1993).

Gerrity, T.R., et al., "Calculated Deposition of Inhaled Particles in the Airway Generations of Normal Subjects," *J. Appl. Phys.,* 47(4):867-873 (1979).

Gonda, I., "Preface. Major Issues and Future Prospects in the Delivery of Therapeutic and Diagnostic Agents to the Respiratory Tract," *Adv. Drug Del. Rev.* 5:1-9 (1990).

Gonda, I., "Targeting by Deposition," in *Pharmaceutical Inhalation Aersol Technology* (ed. A.J. Hickey), Marcel Dekkar Inc., pp. 61-82, New York (1992).

Gurny, R., et al., "Bioadhesive Intraoral Release Systems: Design, Testing and Analysis," *Biomaterials,* 5:336-340 (1984).

Heyder, J., and G. Rudolf, "Mathematical models of particle deposition in the human respiratory tract," *J. Aerosol Sci.*, 15:697-707 (1984).

Heyder, J., et al., "Total Deposition of Aerosol Particles in the Human Respiratory Tract for Nose and Mouth Breathing," *J. Aerosol Sci.*, 6:311-328 (1975).

Hickey, A.J., et al., "Use of Particle Morphology to Influence the Delivery of Drugs from Dry Powder Aerosols," *J. Biopharmaceutical Sci.*, 3(1/2):107-113 (1992).

Hirano, S., et al., "Pulmonary Clearance and Toxicity of Zinc Oxide Instilled into the Rat Lung," *Arch. of Toxicology*, 63:336-342 (1989).

Hrkach, et al., "Synthesis of Poly(L-lactic acid-co-L-lysine) Graft Copolymers," *Macromolecules*, 28(13):4736-4739 (1995).

Hrkach, J.S., et al., "Poly(L-Lactic acid-co-amino acid) Graft Copolymers: A Class of Functional Biodegradable Biomaterials" in Hydrogels and Biodegradable Polymers for Bioapplications, ACS Symposium Series No. 627, Raphae M. Ottenbrite, et al., Eds., Americal Chemical Society, Chapter 8, pp. 93-101, 1996.

Illum, L., et al., "Bioadhesive Microspheres as a Potential Nasal Drug Delivery System," *Int. J. of Pharm.* 39:189-199 (1987).

Johnson, M.A., et al. "Delivery of Albuterol and Ipratrophiumbromide from Two Nebulizer Systems in Chronic Stable Asthma: Efficacy and Pulmonary Deposition," *Chest*, 96:6-10 (1989).

Kao, Y.J., and R.L. Juliano, "Interactions of Liposomes with the Reticuloendothelial System, Effects of Reticuloendothelial Blockade on the Clearance of Large Unilamellar Vesicles," *Biochimica et Biophys. Acta.* 677:453-461 (1981).

Kassem, N.M., and D. Ganderton, "The Influence of Carrier Surface on the Characteristics of Inspirable Powder Aerosols," *J. Pharm. Pharmacol.*, 42(Supp):11 (1990).

Kobayashi, S. et al., "Pulmonary Delivery of Salmon Calcitonin Dry Powders Containing Absorption Enhancers in Rats," *Pharm. Res.*, 13(1):80-83 (1996).

Kohler, D., "Aerosols for Systemic Treatment" *Lung*, Suppl: pp. 677-684 (1990).

Komada, F. et al., Intratracheal Delivery of Peptide and Protein Agents: Absorption from Solution and Dry Powder by Rat Lung, *J. Pharm. Sci.*, 83(6): 863-867 (Jun., 1994).

Kricheldorf, H.R. "α-Aminoacid-N-Carboxy-Anhydrides and Related Heterocycles," Springer-Verlag, Berlin (1987).

Kwok, K.K., et al., "Production of 5-15 μm Diameter Alginate Polylysine Microcapsules by an Air Atomization Technique," Pharm. Res., 8(3):341-344 (1991).

Lai, Y-L., et al., "Sustained Bronchodilation with Isoproterenol Poly(Glycolide-co-Lactide) Microspheres," *Pharm. Res.*, 10(1):119-125 (1993).

Lai, W.C., et al., "Protection Against *Mycoplasma pulminosis* Infection by Genetic Vaccination," *DNA and Cell Biology*, 14(7):643-651 (1995).

Landahl, "On The Removal of Air-borne Droplets by The Human Respiratory Tract: I. The Lung," *Bull. Math. Biophys.*, 12:43-56 (1950).

Langer, R., "New Methods of Drug Delivery", *Science*, 249:1527-1533 (1990).

Le Corre, P., et al., "Preparation and Characterization of Bupivacaine-Loaded Polylactide and Polylactide-Co-Glycolide Microspheres," *Int. J. of Pharmaceutics*, 107:41-49 (1994).

Leone-Bay, A., et al., "Microsphere Formation in a Series of Derivatized α-Amino Acids: Properties, Molecular Modeling, and Oral Delivery of Salmon calcitonin," *J. of Med. Chem.*, 38(21):4257-4262 (1995).

Liu, F., et al., "Pulmonary Delivery of Free and Liposomal Insulin," *Pharm. Res.* 10(2):228-232 (1993).

Liu, W.R., et al., "Moisture-Induced Aggregation of Lyophilized Proteins in the Solid State," *Biotechnol. and Bioeng.*, 37:177-184 (1991).

Martonen, T.B., "Mathematical Model for the Selective Deposition of Inhaled Pharmaceuticals", *J. of Pharm. Sci.*, 82(12):1191-1198 (1993).

Masinde, L.E., and Hickey, A.J., "Aerosolized Aqueous Suspensions of Poly(L-Lactic Acid) Microspheres," *Int. J. of Pharmaceutics*, 100:123-131 (1993).

Mathiowitz, E., et al., "Novel Microcapsules for Delivery Systems," *Reactive Polymers*, 6:275-283 (1987).

Mathiowitz, E., et al., "Polyanhydride Microspheres. IV. Morphology and Characterization of Systems Made by Spray Drying," *J. of Appl. Polymer Sci.* 45:125-134 (1992).

Mathiowitz, E., et al., "Morphology of Polyanhydride Microsphere Delivery Systems," *Scanning Microscopy*, 4 (2):329-340 (1990).

Mathiowitz, E., and R. Langer, "Polyanhydride Microspheres as Drug Carriers I. Hot-Melt Microencapsulation," *J. of Controlled Release* 5:13-22 (1987).

Mathiowitz, E., et al., "Polyanhydride Microspheres as Drug Carriers. II. Microencapsulation by Solvent Removal," *J. of Appl. Polymer Sci.*, 35:755-774 (1988).

Ménache, M.G., et al., "Particle Inhalability Curves for Humans and Small Laboratory Animals," *Annals of Occupational Hygiene*, 39(3):317-328 (1995).

Morimoto, Y., and Adachi, Y., "Pulmonary Uptake of Liposomal Phosphatidylcholine Upon Intratracheal Administration to Rats," *Chem. Pharm. Bull.* 30(6):2248-2251 (1982).

Mulligan, R.C., "The Basic Science of Gene Therapy", *Science*, 260:926-932 (1993).

Newman, S.P., "Therapeutic Inhalation Agents and Devices," *Inhalation Therapy*, 76(5):194-207 (1984).

Newman, S.P., "Aerosol Deposition Considerations in Inhalation Therapy," *Chest*, 88(2):152S-160S (1985).

Niven, R.W., et al., "The Pulmonary Absorption of Aerosolized and Intratracheally Instilled rhG-CSF and monoPEGylated rhG-CSF," *Pharm. Res.*, 12(9):1343-1349 (1995).

Niven, R.W., et al., "Solute Absorption From the Airways of the Isolated Rat Lung. III. Absorption of Several Peptidase-Resistant, Synthetic Polypeptides: Poly-(2-Hydroxyethyl)-Aspartamides," *Pharm. Res.*, 7(10):990-994 (1990).

Niwa, T., et al., "Aerosolization of Lactide/Glycolide Copolymer (PLGA) Nanospheres for Pulmonary Delivery of Peptide-Drugs," *Yakugaku Zasshi*, 115(9):732-741 (1995).

Ogiwara, M., "Clearance and Maximum Removal Rate of Liposomes in Normal and Impaired Liver of Rat," *Gastroenterologia Japonica*, 19(1):34-40 (1984).

Okumura, K., et al., "Intratracheal Delivery of Insulin. Absorption from Solution and Aerosol by Rat Lung," *Int. J. Pharmaceutics*, 88:63-73 (1992).

Patton, J.S., et al., "Bioavailability of pulmonary delivered peptides and proteins: α-interferon, calcitonins and parathyriod hormones," *J. Controlled Release*, 28:79-85 (1994).

Pavia, D., "Lung Mucociliary Clearance". In *Aerosols and the Lung: Clinical and Experimental Aspects*, Clarke, S.W. and Pavia, D., eds.(Butterworths, London), pp. 127-155, (1984).

Peart, J. et al., "Multicomponent Particle Interactions in Dry Powder Aerosols," *J. Pharm. Res.* 14(11 Suppl):p S142-S143 (Nov. 1997).

Pinkerton, K.E., et al., "Aerosolized Fluorescent Microspheres Detected in the Lung Using Confocal Scanning Laser Microscopy", *Microscopy Res. and Tech.*, 26: 437-443 (1993).

Rudt, S., and R.H. Muller, "In Vitro Phagocytosis Assay of Nano- and Microparticles by Chemiluminescence. I. Effect of Analytical Parameters, Particle Size and Particle Concentration," *J. Contr. Rel.*, 22:263-271 (1992).

Rudt, S., et al., "In Vitro Phagocytosis Assay of Nano- and Microparticles by Chemiluminescence. IV. Effect of Surface Modification by Coating of Particles with Poloxamine and Antarox CO on the Phagocytic Uptake", *J. of Contr. Rel.* 25:123-132 (1993).

Ruffin, R.E., et al., "The Preferential Deposition of Inhaled Isoproterenol and Propranolol in Asthmatic Patients," *Chest* 80(6):904-907 (1981).

Sela, M., et al., "Multichain Polyamino Acids," *J. Am. Chem. Soc.*, 78:746-751 (1956).

Smith, A.L., and B. Ramsey, "Aerosol Administration of Antibiotics," *Respiration, 62(suppl 1)* :19-24 (1995).

Smith, P.L., "Peptide Delivery via the Pulmonary Route: A Valid Approach for Local and Systemic Delivery," *J. of Contr. Rel.*, 46:99-106 (1997).

Strand, S.E., and L. Bergqvist, "Radiolabeled Colloids and Macromolecules in the Lymphatic System," *Critical Reviews in Therapeutic Drug Carrier Systems*, 6(3):211-238 (1989).

Swift, D., "The Oral Airway—A Conduit or Collector for Pharmaceutical Aerosols?" *Respiratory Drug Delivery IV*, 187-195 (1994).

Tabata, Y., et al., "Controlled Delivery Systems for Proteins Using Polyanhydride Microspheres," *Pharm. Res.* 10(4): 487-496 (1993).

Tabata, Y., and Y. Ikada, "Effect of Surface Wettability of Microspheres on Phagocytosis," *J. of Colloid and Interface Sci.*, 127(1):132-140 (1989).

Tabata, Y., and Y. Ikada, "Macrophage Phagocytosis of Biodegradable Microspheres Composed of L-lactic Acid/glycolic Acid Homo- and Copolymers,"*J. of Biomed. Mater. Res.*, 22:837-858 (1988).

Tabata, Y., and Ikada, Y., "Effect of Size and Surface Charge of Polymer Microspheres on Their Phagocytosis by Macrophage," *J. Biomed. Mater. Res.*, 22:837-843 (1988).

Taburet, A.M., and Schmit, B., "Pharmacokinetic Optimisation of Asthma Treatment," *Clin. Pharmacokinet.* 26(5):396-418 (1994).

Tansey, I.P., "The Challenges in the Development of Metered Dose Inhalation Aerosols Using Ozone-Friendly Propellants," *Spray Technol. & Market*, 4:26-29 (1994).

Timsina, M.P., et al., "Drug Delivery to the Respiratory Tract Using Dry Powder Inhalers," *Int. J. of Pharm.*, 101: 1-13 (1994).

Turner, J.R., and S.V. Hering, "Greased and Oiled Substrates as Bounce-Free Impaction Surfaces," *J. Aerosol Sci.*, 18(2): 215-224 (1987).

Wall, D.A., "Pulmonary Absorption of Peptides and Proteins," *Drug Delivery*, 2:1-20 (1995).

Warheit, D.B., and Hartsky, M.A., "Role of Alveolar Macrophage Chemotaxis and Phagocytosis in Pulmonary Clearance to Inhaled Particles: Comparisons Among Rodent Species," *Microscopy Res. and Tech.*, 26:412-422 (1993).

Weiner, Norman et al., "Liposomes as a Drug Delivery System," *Drug Development and Industrial Pharmacy, 15 (10)*:1523-1554 (1989).

Wheatley,M.A., et al., "Contrast Agents for Diagnostic Ultrasound: Development and Evaluation of Polymer-Coated Microbubbles," *Biomaterials* 11:713-717 (1990).

Wichert, B., and Rohdewald, P., "Low Molecular Weight PLA: A Suitable Polymer for Pulmonary Administered Microparticles?," *J. Microencapsulation, 10*(2):195-207 (1993).

Wong, M., and Suslick, K.S., "Sonochemically Produced Hemoglobin Microbubbles," *Mat. Res. Soc. Symp. Proc.*, 372:89-95 (1995).

Zanen, P., et al., "The Optimal Particle Size for β-adrenergic Aerosols in Mild Asthmatics", *Int. J. of Pharm.*, 107:211-217 (1994).

Zanen, P., et al., "The Optimal Particle Size for Parasympatholytic Aerosols in Mild Asthmatics", *Int. J. of Pharm.*, 114:111-115 (1995).

Zeng, X.M., et al., "The Controlled Delivery of Drugs to the Lung," *Int. J. of Pharm.*, 124:149-164 (1995).

Zeng, X.M., et al., "Tetrandrine Delivery to the Lung: The Optimisation of Albumin Microsphere Preparation by Central Composite Design," *Int. J. of Pharm.*, 109:135-145 (1994).

\* cited by examiner

STABLE SPRAY-DRIED PROTEIN FORMULATIONS

RELATED APPLICATION(S)

This application claims the benefit of provisional Application Ser. No. 60/097,796, filed Aug. 25, 1998.

BACKGROUND OF THE INVENTION

Aerosols for the delivery of therapeutic agents to the respiratory tract have been described, for example, Adjei, A. and Garren, *J. Pharm. Res.,* 7: 565–569 (1990); and Zanen, P. and Lamm, J.-W. *J. Int. J. Pharm.,* 114: 111–115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems,* 6: 273–313 (1990). The deep lung, or alveoli, are the primary target of inhaled therapeutic aerosols for systemic drug delivery.

Inhaled aerosols have been used for the treatment of local lung disorders including asthma and cystic fibrosis (Anderson, *Am. Rev. Respir. Dis.,* 140: 1317–1324 (1989)) and have potential for the systemic delivery of peptides and proteins as well (Patton and Platz, *Advanced Drug Delivery Reviews,* 8: 179–196 (1992)). However, pulmonary drug delivery strategies present many difficulties for the delivery of macromolecules; these include protein denaturation during aerosolization, excessive loss of inhaled drug in the oropharyngeal cavity (often exceeding 80%), poor control over the site of deposition, lack of reproducibility of therapeutic results owing to variations in breathing patterns, the frequent too-rapid absorption of drug potentially resulting in local toxic effects, and phagocytosis by lung macrophages.

Considerable attention has been devoted to the design of therapeutic aerosol inhalers to improve the efficiency of inhalation therapies. Timsina et. al., *Int. J. Pharm.,* 101: 1–13 (1995); and Tansey, I. P., *Spray Technol. Market,* 4: 26–29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., *J. Aerosol Sci.,* 27: 769–783 (1996). Dry powder formulations ("DPFs") with large particle size have improved flowability characteristics, such as less aggregation (Visser, J., *Powder Technology* 58: 1–10 (1989)), easier aerosolization, and potentially less phagocytosis. Rudt, S. and R. H. Muller, J. *Controlled Release,* 22: 263–272 (1992); Tabata, Y. and Y. Ikada, *J. Biomed. Mater. Res.,* 22: 837–858 (1988). Dry powder aerosols for inhalation therapy are generally produced with mean geometric diameters primarily in the range of less than 5 µm, typically ranging from 1 to 5 µm. Ganderton, D., *J. Biopharmaceutical Sciences,* 3: 101–105 (1992); and Gonda, I. "Physico-Chemical Principles in Aerosol Delivery," in *Topics in Pharmaceutical Sciences* 1991, Crommelin, D. J. and K. K. Midha, Eds., Medpharm Scientific Publishers, Stuttgart, pp. 95–115, 1992. Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.,* 27: 769–793 (1996).

The human lungs can remove or rapidly degrade, for example by hydrolysis or hydrolytic cleavage, deposited aerosols over periods ranging from minutes to hours. In the upper airways, ciliated epithelia contribute to the "mucociliary escalator" by which particles are swept from the airways toward the mouth. Pavia, D. "Lung Mucociliary Clearance," in *Aerosols and the Lung: Clinical and Experimental Aspects,* Clarke, S. W. and Pavia, D., Eds., Butterworths, London, 1984. Anderson, *Am. Rev. Respir. Dis.,* 140: 1317–1324 (1989). In the deep lungs, alveolar macrophages are capable of phagocytosing particles soon after their deposition. Warheit, M. B. and Hartsky, M. A., *Microscopy Res Tech.;* 26: 412–422 (1993); Brain, J. D., "Physiology and Pathophysiology of Pulmonary Macrophages," in *The Reticuloendothelial System,* S. M. Reichard and J. Filkins, Eds., Plenum, N. Y., pp. 315–327, 1985; Dorries, A. M. and Valberg, P. A., *Am. Rev. Resp. Disease* 146: 831–837 (1991); and Gehr, P., *Microscopy Res. and Tech.,* 26: 423–436 (1993). As the diameter of particles exceeds 3 µm, there is increasingly less phagocytosis by macrophages. Kawaguchi, H., *Biomaterials* 7: 61–66 (1986); Krenis, L. J. and Strauss, B., *Proc. Soc. Exp. Med.,* 107: 748–750 (1961); and Rudt, S. and Muller, R. H., *J. Contr. Rel.,* 22: 263–272 (1992). However, increasing the particle size also has been found to minimize the probability of particles (possessing standard mass density) entering the airways and acini due to excessive deposition in the oropharyngeal or nasal regions. Heyder, J., *J. Aerosol Sci.,* 17: 811–825 (1986).

Local and systemic inhalation therapies can often benefit from a relatively slow controlled release of the therapeutic agent. Gonda, I., "Physico-chemical principles in aerosol delivery," in: *Topics in Pharmaceutical Sciences* 1991, D. J. A. Crommelin and K. K. Midha, Eds., Stuttgart: Medpharm Scientific Publishers, pp. 95–117 (1992). Slow release from a therapeutic aerosol can prolong the residence of an administered drug in the airways or acini, and diminish the rate of drug appearance in the bloodstream. Also, patient compliance is increased by reducing the frequency of dosing. Langer, R., *Science,* 249: 1527–1533 (1990); and Gonda, I., "Aerosols for delivery of therapeutic and diagnostic agents to the respiratory tract," in *Critical Reviews in Therapeutic Drug Carrier Systems* 6: 273–313 (1990).

Controlled release drug delivery to the lung may simplify the way in which many drugs are taken. Gonda, I., *Adv. Drug Del. Rev.,* 5: 1–9 (1990); and Zeng, X., et al., *Int. J. Pharm.,* 124: 149–164 (1995). Pulmonary drug delivery is an attractive alternative to oral, transdermal, and parenteral administration because self-administration is simple, the lungs provide a large mucosal surface for drug absorption, there is no first-pass liver effect of absorbed drugs, and there is reduced enzymatic activity and pH mediated drug degradation compared with the oral route. Relatively high bioavailability of many molecules, including macromolecules, can be achieved via inhalation. Wall, D. A., *Drug Delivery,* 2: 1–20 1995); Patton, J. and Platz, R., *Adv. Drug Del. Rev.,* 8: 179–196 (1992); and Byron, P., *Adv. Drug. Del. Rev.,* 5: 107–132 (1990). As a result, several aerosol formulations of therapeutic drugs are in use or are being tested for delivery to the lung. Patton, J. S., et al., *J. Controlled Release,* 28: 79–85 (1994); Damms, B. and Bains, W., *Nature Biotechnology* (1996); Niven, R. W., et al., *Pharm. Res.,* 12(9): 1343–1349 (1995); and Kobayashi, S., et al., *Pharm. Res.,* 13(1): 80–83 (1996).

Drugs currently administered by inhalation come primarily as liquid aerosol formulations. However, many drugs and excipients, especially proteins, peptides (Liu, R., et al., *Biotechnol. Bioeng.,* 37: 177–184 (1991)), and biodegradable carriers such as poly(lactide-co-glycolides) (PLGA), are unstable in aqueous environments for extended periods of time. This can make storage as a liquid formulation problematic. In addition, protein denaturation can occur during aerosolization with liquid formulations. Mumenthaler, M., et al., *Pharm. Res.,* 11: 12–20 (1994). Considering these and other limitations, dry powder formulations (DPF's) are gaining increased interest as aerosol formulations for pulmonary delivery. Damms, B. and W. Bains, *Nature Biotechnology* (1996); Kobayashi, S., et al., *Pharm. Res.,* 13(1): 80–83 (1996); and Timsina, M., et al., *Int. J. Pharm.,* 101: 1–13 (1994). However, among the disadvantages of DPF's is that powders of ultrafine particulates usually have poor flowability and aerosolization properties, leading to relatively low respirable fractions of aerosol, which are the fractions of inhaled aerosol that escape deposition in the mouth and throat. Gonda, I., in *Topics in Pharmaceutical Sciences* 1991, D. Crommelin and K. Midha, Editors, Stuttgart: Medpharm Scientific Publishers, 95–117 (1992). A primary concern with many aerosols is particulate aggregation caused by particle—particle interactions, such as hydrophobic, electrostatic, and capillary interactions. An effective dry-powder inhalation therapy for both short and long term release of therapeutics, either for local or systemic delivery, requires a powder that displays minimum aggregation, as well as a means of avoiding or suspending the lung's natural clearance mechanisms until drugs have been effectively delivered.

Particles suitable for delivery to the respiratory system of a patient can be prepared by spray drying from aqueous solutions. A number of proteins, however, denature under aqueous spray drying conditions. In some cases, protein particles which are prepared by spray drying from aqueous solutions tend to be hygroscopic and susceptible to lose their activity at even modest humidity levels.

Spray drying in the presence of polysorbate-20 surfactant has been shown to reduce the aggregation of recombinant growth hormone during spray drying. In another approach, solvents including water and methanol or water and ethanol have been employed to spray dry hollow albumin microcapsules. Neither technique, however, has resulted in both, improved protein stability and reduced protein hygroscopicity.

Therefore, a need exists for methods of producing spray-dried particles which overcome or minimize the above-referenced problems.

SUMMARY OF THE INVENTION

The invention relates to methods of producing spray-dried particles, also referred to herein as particles, which have improved bioactive agent stability.

In one embodiment of the invention the method includes combining a biologically active (bioactive) agent, a phospholipid and an organic-aqueous co-solvent to form a mixture which is spray-dried to produce spray-dried particles having improved bioactive agent stability. In another embodiment of the invention, the method includes combining a bioactive agent, a phospholipid and an organic solvent to form a mixture which is spray-dried to produce particles having improved bioactive agent stability. In a preferred embodiment, the bioactive agent is a therapeutic, prophylactic or a diagnostic agent.

In one embodiment of the invention, the bioactive agent includes peptides. In another embodiment, the bioactive agent includes proteins. In a further embodiment, the bioactive agent includes biologically active or bioactive macromolecules other than peptides or proteins. In still another embodiment of the invention, the agent includes any combination of peptides, proteins and/or other biologically active macromolecules.

In one embodiment, the phospholipid is present in the spray-dried particle in an amount of at least 1 weight %. In another embodiment, the phospholipid is selected from the group consisting of phosphatidylcholines, phosphatidylethanolamines, phosphatidylglycerols, phosphatidylserines, phosphatidylinositols and combinations thereof. In yet another embodiment of the invention, the spray dried particles have a tap density less than 0.4 g/cm$^3$.

The invention also relates to a method including administering an effective amount of the spray-dried particles obtained by the methods of the invention to the respiratory tract of a patient in need of treatment, prophylaxis or diagnosis.

The spray dried particles can be used for enhanced delivery of a therapeutic, prophylactic or diagnostic agent to the airways or the alveolar region of the lung. The particles may be effectively aerosolized for administration to the respiratory tract to permit systemic or local delivery of a wide variety of therapeutic agents. They also optionally may be co-delivered with larger carrier particles, not carrying a therapeutic agent, having, for example, a mean diameter ranging between about 50 $\mu$m and 100 $\mu$m. The particles can be used to form a composition that includes the particles and a pharmaceutically acceptable carrier for administration to a patient, preferably for administration via inhalation.

According to one embodiment of the invention, the spray-dried particles can themselves be used as carriers for the delivery of a therapeutic, prophylactic or diagnostic agent to the pulmonary system. According to this embodiment of the invention, a therapeutic, prophylactic or diagnostic agent can be added onto the spray-dried carrier particles for delivery to the pulmonary system. Small-sized therapeutic, prophylactic or diagnostic agents, such as, for example, agents having a particle size in the nanometer range, can be carried by the spray-dried carrier particles and delivered to the pulmonary system.

By providing a method for producing spray-dried particles which have increased protein stability, the invention has numerous advantages. In addition, it provides a method for producing aerodynamically light particles suitable for delivery to the respiratory system.

DETAILED DESCRIPTION OF THE INVENTION

The features and other details of the invention, either as steps of the invention or as combination of parts of the invention, will now be more particularly described and pointed out in the claims. It will be understood that the particular embodiments of the invention are shown by way of illustration and not as limitations of the invention. The principle feature of this invention may be employed in various embodiments without departing from the scope of the invention.

The invention generally relates to methods of producing spray-dried particles which have improved bioactive agent stability. The terms "bioactive" and "biologically active" are used herein interchangeably. As used herein the term bioactive agent includes peptides and proteins. Proteins are defined herein as having about 100 amino acid residues or more, while peptides are defined herein as having less than about 100 amino acid residues. As used herein, the term bioactive agent also includes bioactive macromolecules other than peptides or proteins. Examples of such bioactive macromolecules include, but are not limited to: polysaccharides and other sugars, lipids, DNA, RNA, nucleic acid sequences, genes, antisense molecules, antigens and others. In a preferred embodiment of the invention, the bioactive agent can be a therapeutic, prophylactic or diagnostic agent.

Specific examples of preferred biologically active agents which can be employed in the method of the invention include but are not limited to: insulin, erythroprotein, interferons, colony stimulating factors, such as, granulocyte colony stimulating factor, growth hormones, such as, for example, human growth hormone, LHRH analogs, LHRH antagonists, tissue plasminogen activator, somatostatin analog, r Factor VIII, r Factor IX, calcitonin, abciximab, dornase alfa, polysaccharides, AG337, bone inducing protein, bone morphogenic protein, brain derived growth factor, gastrin 17 immunogen, interleukins, such as, for example, IL-2, PEF superoxide, infliximab, permeability increasing protein-21$_R$, platelet derived growth factor, stem cell factor, Thyrogen$^R$ and somatomedin C.

As used herein, the term stability generally is related to maintaining the integrity or to minimizing the denaturation, aggregation or unfolding of a biologically active agent such as a protein, peptide or another bioactive macromolecule after being exposed to conditions known to negatively affect its stability. As used herein, improved stability generally means that, under conditions known to result in degradation, denaturation, aggregation or unfolding, the bioactive agent maintains greater stability compared to control particles subjected to the same conditions. Control particles can be, for example, commercially available particles or powders which include the bioactive agent. For example, control particles can include lyophilized bulk proteins or lyophilized sugars. Control particles can also be particles obtained by methods other than the methods of the invention. For example, control particles can include particles that are spray-dried from aqueous solutions or particles that do not include a phospholipid.

Protein degradation, for example, is often facilitated by water. Improved protein stability can be demonstrated in terms of improved retention of protein integrity under storage conditions at specified moisture levels. For example, spray-dried particles having improved protein stability are particles which undergo less degradation, denaturation, aggregation and/or unfolding, relative to protein formulations spray-dried from aqueous solutions, or spray-dried from mixtures that do not include a phospholipid, after storage for six weeks at about 25° C. (e.g. +/−2° C.) and about 60% (e.g. +/−5%) relative humidity. If more severe conditions are employed, spray-dried particles having improved protein stability are particles which, after storage for six weeks at about 40° C. (e.g. +/−2° C.) and about 75% (e.g. +/−5%) relative humidity, retain greater protein stability (or undergo less degradation, denaturation, aggregation and/or unfolding) compared to protein formulations spray-dried from aqueous solutions or spray-dried from mixtures that do not include a phospholipid. In one embodiment of the invention the spray-dried particles retain at least about 70%, preferably at least about 80% protein integrity, when stored at about 25° C. and about 60% relative humidity conditions for six weeks. In another embodiment of the invention the spray-dried particles retain at least about 50%, preferably at least about 60% protein integrity when stored at about 40° C. and about 75% relative humidity conditions for six weeks.

Bioactive agent stability or integrity can be measured by techniques such as those known in the art. For example, protein stability can be measured by size exclusion high performance liquid chromatography (SEC HPLC). Other suitable techniques for detecting bioactive agent stability, aggregation or degradation include, but are not limited to: reverse phase high performance liquid chromatography (RP HPLC); sodium dodecyl sulfate polyacrylamide gel electrophoresis (SDS PAGE); enzyme-linked immunoadsorbent assay (ELISA) and radioimmunoassay (RIA).

In one embodiment, the method for producing spray-dried particles having improved bioactive agent stability includes combining a bioactve agent, such as, for example, the agents described above, with a phospholipid and a co-solvent to form a mixture.

Co-solvents include an aqueous solvent and an organic solvent. Suitable organic solvents that can be employed include but are not limited to alcohols such as, for example, ethanol, methanol, propanol, isopropanol and butanols. Other organic solvents include but are not limited to perfluorocarbons, dichloromethane, chloroform, ether, ethyl acetate, methyl tert-butyl ether and others. Aqueous solvents include water and buffered solutions. In a preferred embodiment, the organic solvent is ethanol.

Preferably, the amount of organic solvent can be present in the co-solvent in an amount ranging from about 50 to about 90% by volume. In a more preferred embodiment, the organic solvent is present in the co-solvent in an amount ranging from about 60 to about 85% by volume.

In another embodiment, the method for producing spray-dried particles having improved bioactive agent stability includes combining a bioactive agent, such as, for example, the agents described above, with a phospholipid and an organic solvent to form a mixture. The organic solvent includes but is not limited to the organic solvents described above.

In a preferred embodiment of the invention, the phospholipid, also referred to herein as phosphoglyceride, is a phospholipid endogenous to the lung. Such a phospholipid is particularly advantageous in preparing spray-dried particles suitable for delivery to the respiratory system of a patient.

In another preferred embodiment the phospholipid is selected from the group consisting of phosphatidylcholines, phosphatidylethanolamines, phosphatidylglycerols, phosphatidylserines, phosphatidylinositols and combinations thereof. Specific examples of phospholipids include but are not limited to phosphatidylcholines dipalmitoyl phosphatidylcholine (DPPC), dipalmitoyl phosphatidylethanolamine (DPPE), distearoyl phosphatidylcholine (DSPC), dipalmitoyl phosphatidyl glycerol (DPPG) or any combinations thereof.

The mixture can have a neutral, acidic or alkaline pH. Optionally, a pH buffer can be added to the solvent or co-solvent or to the formed mixture. Preferably, the pH can range from about 3 to about 10.

The mixture obtained by combining the bioactive agent with the phospholipid and the co-solvent is spray-dried. Suitable spray-drying techniques are described, for example, by K. Masters in "Spray Drying Handbook", John Wiley & Sons, New York, 1984. Generally, during spray-drying, heat from a hot gas such as heated air or nitrogen is used to evaporate the solvent from droplets formed by atomizing a continuous liquid feed.

In a preferred embodiment, a rotary atomizer is employed. Examples of suitable spray driers using rotary atomization include Niro spray drier Mobile Minor.

In one embodiment of the invention, the phospholipid, is present in the spray-dried particles in an amount of at least about 1 weight %. In another embodiment, the phospholipid is present in the particles in an amount ranging from about 1% to about 99%, preferably from about 10% to about 70% by weight. The amount of phospholipid to be included in the particles can be determined experimentally by determining the amount of phospholipid which, when included in the spray-dried particles, results in improved stability, measured by means such as, but not limited to, those described above.

The bioactive agent can be present in the spray-dried particles of the invention in an amount ranging from about 1 to about 99 weight %, preferably from about 30 to about 90 weight %. In one embodiment, the spray-dried particles include a protein, which is present in the particles in an amount ranging from about 1 to about 99 weight %, preferably in an amount ranging from about 30 to about 90 weight %.

Without being held to any particular mechanism, it is believed that the improved stability is at least in part the result of a lowered tendency of the protein to be situated at the air-water interface or air-co-solvent interface of the droplet. The phospholipid is believed to compete with the protein for the air-droplet interface, thereby protecting the protein. Furthermore, it is believed that the presence of the phospholipid also renders the spray-dried particles less prone to degradation owing to exposure to high humidity conditions during storage.

In a preferred embodiment, the spray-dried particles consist of bioactive agent and phospholipid. For example, the spray-dried particles include only the bioactive agent, such as, for example, the proteins, peptides or bioactive macromolecule or any mixtures thereof described above and a phospholipid, such as, for example, the phospholipids described above. In some instances, the bioactive agent can be in the form of a complex between the charged agent and a molecule of opposite charge. This can be the case for many proteins. The molecule of opposite charge can be a charged lipid or an oppositely charged protein. The molecule of the opposite charge can also be a cation such as $Ca^{++}$ or $Zn^{++}$. Charged zinc cations in relation to recombinant human growth hormone are discussed, for example, by Y.-F. Maa et al., in *J. Pharmaceutical Sciences*, Vol. 87(2), pp. 152–159 (1998). If the agent to be delivered is negatively charged (such as insulin), protamine or other positively charged molecules can be added to provide a lipophilic complex which results in the sustained release of the negatively charged agent. Negatively charged molecules can be used to render insoluble positively charged agents.

In another embodiment of the invention, the particles consist essentially of bioactive agent and phospholipd. For example the spray-dried particles can further include small or trace amounts of residual solvent or co-solvent, impurities, substances which control the pH, or other materials in small or trace amounts. Ranges for impurity levels and for residual solvent levels are generally well established in the industry and known to those skilled in the art. Amounts of pH buffers that can be added to the solvent, co-solvent or mixture are also known in the art.

Alternatively, the spray-dried particles can include materials in addition to the compounds discussed above. For example, the spray dried particles can include excipients such as, for example, a sugar, such as lactose, amino acids, surfactants or buffer salts, polysaccharides, cyclodextrins and others.

The spray-dried particles of the invention can also include one or more compounds employed in controlled or sustained release formulations. For example, the spray-dried particles can include a biocompatible, and preferably biodegradable polymer, copolymer, or blend. Preferred polymers are those which are capable of forming aerodynamically light particles having a tap density less than about 0.4 $g/cm^3$, a mean diameter between about 5 μm and about 30 μm and an aerodynamic diameter between about one and about five microns, preferably between one and three microns. The polymers may be tailored to optimize different characteristics of the particle including: i) interactions between the bioactive agent to be delivered and the polymer to provide stabilization of the bioactive agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides can be used to form the particles. For example, polyanhydrides such as poly[(ρ-carboxyphenoxy)-hexane anhydride] (PCPH) may be used. Suitable biodegradable polyanhydrides are described in U.S. Pat. No. 4,857,311.

In another embodiment, bulk eroding polymers such as those based on polyesters including poly(hydroxy acids) can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(D,L-lactic-co-glycolic acid) ("PLGA") which incorporate a surfactant such as DPPC.

Still other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

In one embodiment, the particles include functionalized polyester graft copolymers, as described in Hrkach et al., *Macromolecules*, 28: 4736–4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications*, ACS Symposium Series No. 627, Raphael M. Ottenbrite et al., Eds., American Chemical Society, Chapter 8, pp. 93–101, 1996.

Materials other than biodegradable polymers can be included in the spray-dried particles of the invention. Suitable materials include various non-biodegradable polymers and various excipients.

The spray-dried particles of the invention can also include surfactants such as, for example, hexadecanol; fatty alcohols such as polyethylene glycol (PEG); polyoxyethylene-9-lauryl ether; a surface active fatty acid, such as palmitic acid or oleic acid; glycocholate; surfactin; a poloxomer; a sorbitan fatty acid ester such as sorbitan trioleate (Span 85); tyloxapol and a phospholipid.

As used herein, the term "surfactant" refers to any compound which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

As used herein, a particle "incorporating a surfactant" refers to a particle with a surfactant on at least the surface of the particle. The surfactant may be incorporated throughout the particle and on the surface during particle formation, or may be coated on the particle after particle formation. The surfactant can be coated on the particle surface by adsorption, ionic or covalent attachment, or physically "entrapped" by the surrounding matrix. The surfactant can be, for example, incorporated into controlled release particles, such as polymeric microspheres.

The spray-dried particles of the invention can further include a therapeutic, prophylactic or diagnostic compound or drug other than the bioactive agent described above. Examples of therapeutic, prophylactic or diagnostic compounds or drugs include, but are not limited to drugs for the treatment or prophylaxis of asthma, enthesima, cystic fibrosis or for systemic treatment. Antiviral, antibacterial or antifungal drugs can be also included as can be diagnostic or prophylactic agents such as known to in the art. Other examples of suitable therapeutic, prophylactic or diagnostic drugs or compounds, other than the bioactive agent described above, which can be included in the particles, can be found in U.S. Pat. No. 5,855,913, to Hanes et al, issued Jan. 5, 1999, the contents of which are incorporated herein by reference in their entirety.

In a preferred embodiment, the spray-dried particles have a tap density less than about 0.4 g/cm$^3$. In another embodiment, the spray-dried particles have a tap density less than about 0.1 g/cm$^3$. In yet another embodiment, the spray-dried particles have a tap density less than about 0.05 g/cm$^3$.

As used herein, the phrase "aerodynamically light particles" refers to particles having a tap density less than about 0.4 g/cm$^3$. The tap density of particles of a dry powder may be obtained using a GeoPyc™ instrument (Micrometrics Instrument Corp., Norcross, Ga. 30093). A Dual Platform Microprocessor Controlled Tap Density Tester (Vankel, N.C.) can also be used. Tap density is a standard measure of the envelope mass density. The envelope mass density of an isotropic particle is defined as the mass of the particle divided by the minimum sphere envelope volume within which it can be enclosed. Features which can contribute to low tap density include irregular surface texture and porous structure.

The preferred median diameter for aerodynamically light particles for inhalation therapy is at least about 5 microns ($\mu$m), for example between about 5 and about 30 $\mu$m. In a preferred embodiment, the spray-dried particles have a median geometric diameter of between about 5 $\mu$m and about 30 $\mu$m. Terms such as median diameter, mass median diameter (MMD), mass median geometric diameter (MMGD) and mass median envelope diameter (MMED) are herein used interchangeably. The term diameter, in contrast with the term "aerodynamic diameter", refers herein to mass or geometric diameter. The terms "aerodynamic diameter" and "mass median aerodynamic diameter" (MMAD) are used herein interchangeably. In one embodiment of the invention, the mass median aerodynamic diameter is between about 1 $\mu$m and about 5 $\mu$m. In another embodiment of the invention, the mass median aerodynamic diameter is between about 1 $\mu$m and about 3 $\mu$m. In another embodiment, the mass median aerodynamic diameter is between about 3 $\mu$m and about 5 $\mu$m.

The mass median diameter of the spray-dried particles can be measured using an electrical zone sensing instrument such as Coulter Multisizer Ile (Coulter, Miami, Fla.) or a laser diffraction instrument (for example a Helos instrument manufactured by Sympatec, Princeton, N.J.). The diameter of particles in a sample will range depending upon factors such as particle composition and methods of synthesis. The distribution of size of particles in a sample can be selected to permit optimal deposition within targeted sites within the respiratory tract.

Aerodynamically light particles may be fabricated or separated, for example by filtration or centrifugation, to provide a particle sample with a preselected size distribution. For example, greater than 30%, 50%, 70%, or 80% of the particles in a sample can have a diameter within a selected range of at least about 5 $\mu$m. The selected range within which a certain percentage of the particles must fall may be for example, between about 5 and about 30 $\mu$m, or optionally between about 5 and about 15 $\mu$m. In one preferred embodiment, at least a portion of the particles have a diameter between about 9 and about 11 $\mu$m. Optionally, the particle sample also can be fabricated wherein at least about 90%, or optionally about 95% or about 99%, have a diameter within the selected range. The presence of the higher proportion of the aerodynamically light, larger diameter particles in the particle sample enhances the delivery of therapeutic or diagnostic agents incorporated therein to the deep lung. Large diameter particles generally mean particles having a median geometric diameter of at least about 5 $\mu$m.

Aerodynamically light particles with a tap density less than about 0.4 g/cm$^3$, median diameters of at least about 5 $\mu$m, and an aerodynamic diameter of between about one and about five microns, preferably between about one and about three microns, are more capable of escaping inertial and gravitational deposition in the oropharyngeal region, and are targeted to the airways or the deep lung. The use of larger, more porous particles is advantageous since they are able to aerosolize more efficiently than smaller, denser aerosol particles such as those currently used for inhalation therapies.

In comparison to smaller, relatively denser particles the larger aerodynamically light particles, preferably having a median diameter of at least about 5 $\mu$m, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 $\mu$m. Kawaguchi, H., et al., *Biomaterials* 7: 61–66 (1986); Krenis, L. J. and Strauss, B., *Proc. Soc. Exp. Med.*, 107: 748–750 (1961); and Rudt, S. and Muller, R. H., *J. Contr. Rel.*, 22: 263–272 (1992). For particles of statistically isotropic shape, such as spheres with rough surfaces, the particle envelope volume is approximately equivalent to the volume of cytosolic space required within a macrophage for complete particle phagocytosis.

Aerodynamically light particles thus are capable of a longer term release of an encapsulated agent in the lungs. Following inhalation, aerodynamically light biodegradable particles can deposit in the lungs, and subsequently undergo slow degradation and drug release, without the majority of the particles being phagocytosed by alveolar macrophages. The drug can be delivered relatively slowly into the alveolar fluid, and at a controlled rate into the blood stream, minimizing possible toxic responses of exposed cells to an excessively high concentration of the drug. The aerodynamically light particles thus are highly suitable for inhalation therapies, particularly in controlled release applications.

The particles may be fabricated with the appropriate material, surface roughness, diameter and tap density for localized delivery to selected regions of the respiratory tract such as the deep lung or upper airways. For example, higher density or larger particles may be used for upper airway delivery, or a mixture of varying sized particles in a sample, provided with the same or different therapeutic agent may be administered to target different regions of the lung in one administration. Particles having an aerodynamic diameter in the range from about 3 to about 5 μm are preferred for delivery to the central and upper airways. Particles having an aerodynamic diameter in the range from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26: 293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992)), by the formula:

$$d_{aer}=d\sqrt{\rho}$$

where the envelope mass ρ is in units of g/cm³. Maximal deposition of monodisperse aerosol particles in the alveolar region of the human lung (~60%) occurs for an aerodynamic diameter of approximately $d_{aer}$=3 μm. Heyder, J. et al., *J. Aerosol Sci.*, 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho} \text{ μm (where } \rho<1 \text{ g/cm}^3\text{);}$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology*, 58: 1–10. Thus, large particle size increases efficiency of aerosolization to the deep lung for particles of low envelope mass density, in addition to contributing to lower phagocytic losses.

In one embodiment of the invention, the spray-dried particles have a tap density less than about 0.4 g/cm³ and a median diameter between about 5 μm and about 30 μm, which in combination yield an aerodynamic diameter of between about 1 and about 5 μm, preferably between about 1 and about 3 μm. The aerodyanamic diameter is calculated to provide for maximum deposition within the lungs, previously achieved by the use of very small particles of less than five microns in diameter, preferably between one and three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface.

According to one embodiment of the invention, the particles have a mass density of less than about 0.4 g/cm³ and a mean diameter of between about 5 μm and about 30 μm. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm³ and a mean diameter of between about 5 μm and about 30 μm is between about 1 μm and about 5 μm.

The spray-dried particles can be used for controlled systemic or local delivery of therapeutic or diagnostic agents to the respiratory tract via aerosolization. Administration of the particles to the lung by aerosolization permits deep lung delivery of relatively large diameter therapeutic aerosols, for example, greater than about 5 μm in median diameter. The particles can be fabricated with a rough surface texture to reduce particle agglomeration and improve flowability of the powder. The spray-dried particles have improved aerosolization properties. The spray-dried particle can be fabricated with features which enhance aerosolization via dry powder inhaler devices, and lead to lower deposition in the mouth, throat and inhaler device.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems*, 6: 273–313, 1990; and in Moren, "Aerosol dosage forms and formulations," in: *Aerosols in Medicine. Principles, Diagnosis and Therapy*, Moren, et al., Eds, Esevier, Amsterdam, 1985.

The greater efficiency of aerosolization by the particles disclosed herein relative to particles that do not include a surfactant or a charged complex of a therapeutic agent permits more of a therapeutic agent to be delivered. The use of biodegradable polymers permits controlled release in the lungs and long-time local action or systemic bioavailability. Denaturation of macromolecular drugs can be minimized during aerosolization since macromolecules can be contained and protected within a polymeric shell. Coencapsulation of peptides with peptidase-inhibitors can minimize peptide enzymatic degradation. Pulmonary delivery advantageously can reduce or eliminate the need for injection. For example, the requirement for daily insulin injections can be avoided.

The invention is also related to a method for delivery to the pulmonary system. The method comprises administering to the respiratory tract of a patient in need of treatment, prophylaxis or diagnosis an effective amount of the spray dried particles obtained by the methods of the invention.

Porous or aerodynamically light particles, having a geometric size (or mean diameter) in the range of about 5 to about 30 micrometers, and tap density less than about 0.4 g/cm³, such that they possess an aerodynamic diameter of about 1 to about 3 μm, have been shown to display ideal properties for delivery to the deep lung. Larger aerodynamic diameters, preferably ranging, for example from about 3 to about 5 μm are preferred, however, for delivery to the central and upper airways. According to one embodiment of the invention the particles have a tap density of less than about 0.4 g/cm$^3$ and a mean diameter of between about 5 μm and about 30 μm. According to another embodiment of the invention, the non-polymeric particles have a mass density of less than about 0.4 g/cm$^3$ and a mean diameter of between about 5 μm and about 30 μm. In one embodiment of the invention, the particles have an aerodynamic diameter between about one and about five microns. In another embodiment of the invention, the particles have an aerodynamic diameter between about one and about three microns. In still another embodiment of the invention, the particles have an aerodynamic diameter between about three and about five microns.

For therapeutic, diagnosis or prophylactic use, particles can be delivered from an inhaler device, such as, but not limited to a metered-dose-inhaler (MDI), dry-powder inhaler (DPI) nebulizer or by instillation. Such devices are known in the art. For example, a DPI is described in U.S. Pat. No. 4,069,819 issued to Valentini, et al. on Aug. 5, 1976.

Exemplifications

The present invention will be further understood by reference to the following non-limiting examples.

Some of the methods and materials employed in the following examples are described in U.S. application Ser. No. 09/211,940, filed Dec. 15, 1998, in U.S.
    application Ser. No. 08/739,308, filed Oct. 29, 1996, now U.S. Pat. No. 5,874,064, in U.S. application Ser. No. 08/655,570, filed May 24, 1996, in U.S. application Ser. No. 09/194,068, filed May 23, 1997, in PCT/US97/08895 application filed May 23, 1997, in U.S. application Ser. No. 08/971,791, filed Nov. 17, 1997, in U.S. application Ser. No. 08/784,421, filed Jan. 16, 1997, now U.S. Pat. No. 5,855,913 and in U.S.
    application Ser. No. 09/337,245, filed on Jun. 22, 1999, all of which are incorporated herein by reference in their entirety.

Materials

IgG was obtained from Sigma, St. Louis, Mo. The DNA sequence of hGH is described in U.S. Pat. No. 4,898,830 issued on Feb. 6, 1990 to Goeddel et al. DPPC was obtained from Avanti (Alabaster, ALA) or Sigma.

Spray Drying

A Mobile Minor spray-drier from Niro (Denmark) was used. The hot gas was dehumidified air or nitrogen. The gas temperature ranged from about 80 to about 150° C.

Particle Size Distribution Analysis

Size distributions were determined using a Coulter Multisizer II (Coulter Corp., Miami, Fla.). Approximately 10 drops Coulter type IA non-ionic dispersant were added, followed by 2 mL isoton II solution (Coulter), to 5–10 mg microspheres, and the particles were dispersed by brief vortex mixing. This suspension was added to 50 mL isoton II solution until the coincidence of particles was between 5 and 8%. Greater than 500,000 particles were counted for each batch of spheres.

Particle Morphology by Scanning Electron Microscopy (SEM)

Microsphere morphology was observed by scanning electron microscopy (SEM) using a Stereoscan 250 MK3 microscope from Cambridge Instruments (Cambridge, Mass.) at 15 kV. Microspheres were freeze-dried, mounted on metal stubs with double-sided tape, and coated with gold prior to observation.

Particle Density Analysis

Bulk density was estimated by tap density measurements, such as obtained using a Dual Platform Microprocessor Controlled Tap Density Tester (Vankel, N.C.) and confirmed by mercury intrusion analysis at Porous Materials, Inc. (Ithaca, N.Y.).

Protein Integrity Measurements

Protein integrity measurements were obtained by size exclusion chromatography (SEC-HPLC).

EXAMPLE 1

IgG particles were prepared to demonstrate that particles suitable for inhalation, with theoretical aerodynamic diameter between 1 and 3 microns, could be prepared by spray drying a protein with DPPC in a water/ethanol cosolvent mixture. A 70/30 ethanol/water co-solvent was employed. The solute concentration (combined IgG and DPPC) was 0.1% w/v. The pH of the water varied from 3–5.7. The spray drying parameters were inlet temperature (110° C.), atomizer spin rate (1–2 bar), feed rate of 40 mL/min, and outlet temperature near 50° C. 40/60 IgG/DPPC and 50/50 IgG/DPPC particles were prepared. The tap densities ranged from 0.02 to 0.2 g/cm$^3$ with mean geometric diameters near 7 microns. This gave aerodynamic diameters in the range of 1–3 microns, ideal for inhalation. SDS PAGE analysis showed no difference between starting IgG material and spray dried IgG particle indicating no aggregates or degradation.

EXAMPLE 2

Human growth hormone (hGH) is one example of a protein susceptible to denaturation during spray drying from an aqueous solution. hGH was spray-dried in an aqueous/ethanol co-solvent mixture with DPPC.

A 70/30 ethanol/aqueous co-solvent (vol/vol) and solute concentrations (combined hGH and DPPC) of 0.1% w/v were used. The pH was 7.4 (NaPO$_4$ buffer). The spray drying parameters were as described above. 60/40 hGH/DPPC and 80/20 hGH/DPPC particles were prepared.

The tap densities ranged from 0.02 to 0.04 g/cc with mean geometric diameters of 7–8 microns. This gave aerodynamic diameters in the range of 1–3 microns, ideal for inhalation.

The 60% and 80% hGH spray dried particles were analyzed by HPLC to detect instabilities (e.g. aggregation, deamidation). The spray dried particles described above were compared to hGH particles that were spray dried without the presence of DPPC and an organic co-solvent. The analysis showed a reduction of aggregates from 23% to less than 2%, and no detectable deamidation.

EXAMPLE 3

The stability of hGH protein over an extended period of time (6 weeks) upon exposure to different temperatures and humidities was determined. These experiments were carried out in loosely capped glass vials providing samples to full exposure to temperature and humidity. The conditions selected were harsher than those generally present during product storage.

The stability of hGH was measured by SEC-HPLC which shows the amount of monomer (the active form) and higher molecular weight aggregates. Table 1 presents the SEC-HPLC data demonstrating the better stability of the hGH spray-dried particles (60% hGH and 40% DPPC) versus bulk hGH powder.

TABLE 1

| Stability Condition | % Monomer hGH/DPPC Particles (6 weeks) | % Monomer bulk hGH Powder (6 weeks) |
|---|---|---|
| 25 ± 2° C. & 60 ± 5% RH | 88.9 | 25.4 |
| 40 ± 2° C. & 75 ± 5% RH | 68.4 | 37.1 |

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for producing spray-dried particles having improved stability of a protein comprising:
   (a) combining a protein, a phospholipid, a co-solvent, said co-solvent including an aqueous solvent and an organic solvent, and, optionally, a buffer salt, to form a mixture; and
   (b) spray-drying said mixture to produce spray-dried particles comprising a stabilized protein;
   wherein the particles consist of the stabilized protein, the phospholipid and, optionally, the buffer salt, and wherein the phospholipid is present in the particles in an amount of at least about 10 weight percent.

2. The method of claim 1 wherein the phospholipid is selected from the group consisting of phosphatidylcholines, phosphatidylethanolamines, phosphatidylglycerols, phosphatidylserines, phosphatidylinositols and combinations thereof.

3. The method of claim 1 wherein the protein is human growth hormone.

4. The method of claim 1 wherein the protein is present in the spray-dried particles in an amount ranging from about 1 to about 90 weight %.

5. The method of claim 1 wherein protein stability is measured by SEC-HPLC.

6. The method of claim 1 wherein the spray-dried particles retain at least about 70% protein integrity when stored at about 25° C. and about 60% relative humidity conditions for six weeks.

7. The method of claim 1 wherein the spray-dried particles retain at least about 50% protein integrity when stored at about 40° C. and about 75% relative humidity conditions for six weeks.

8. The method of claim 1 wherein the protein is a therapeutic, prophylactic or diagnostic agent.

9. The method of claim 1 wherein the solute concentration in said mixture is at least 0.1 weight/volume %.

10. The method of claim 1 wherein the co-solvent includes an alcohol.

11. The method of claim 1 wherein the organic solvent is present in the co-solvent in a concentration of at least 50 volume %.

12. The method of claim 1 wherein the spray-dried particles have a tap density less than about 0.4 g/cm$^3$.

13. The method of claim 1 wherein the spray-dried particles have a tap density less than about 0.1 g/cm$^3$.

14. The method of claim 1 wherein the spray-dried particles have a tap density less than about 0.05 g/cm$^3$.

15. The method of claim 1 wherein the spray-dried particles have a median geometric diameter of between about 5 microns and about 30 microns.

16. The method of claim 1 wherein the spray-dried particles have an aerodynamic diameter of between about 1 micron and about 5 micron.

17. The particles produced by the method of claim 1.

18. A method comprising administering to the respiratory tract of a patient in need of treatment, prophylaxis or diagnosis an effective amount of the spray-dried particles produced by the method of claim 1.

19. A method for producing spray-dried particles having improved stability of a peptide comprising:
   (a) combining a peptide, a phospholipid, a co-solvent, said co-solvent including an aqueous solvent and an organic solvent, and, optionally, a buffer salt, to form a mixture; and
   b) spray-drying said mixture to produce spray-dried particles comprising a stabilized peptide;
   wherein the particles consist of the stabilized peptide, the phospholipid and, optionally, the buffer salt, and wherein the phospholipid is present in the particles in an amount of at least about 10 weight percent.

20. A method for producing spray-dried particles having improved stability of a protein comprising:
   (a) combining a protein, a phospholipid, an organic solvent, and optionally, a buffer salt, to form a mixture; and
   (b) spray-drying said mixture to produce spray-dried particles comprising a stabilized protein;
   wherein the particles consist of the stabilized protein, the phospholipid and, optionally, the buffer salt, and wherein the phospholipid is present in the particles in an amount of at least about 10 weight percent.

21. The method of claim 20 wherein the phospholipid is selected from the group consisting of phosphatidylcholines, phosphatidylethanolamines, phosphatidylglycerols, phosphatidylserines, phosphatidylinositols and combinations thereof.

22. The method of claim 20 wherein the protein is human growth hormone.

23. The method of claim 20 wherein the protein is present in the spray-dried particles in an amount ranging from about 1 to about 90 weight %.

24. The method of claim 20 wherein protein stability is measured by SEC-HPLC.

25. The method of claim 20 wherein the spray-dried particles retain at least about 70% protein integrity when stored at about 25° C. and about 60% relative humidity conditions for six weeks.

26. The method of claim 20 wherein the spray-dried particles retain at least about 50% protein integrity when stored at about 40° C. and about 75% relative humidity conditions for six weeks.

27. The method of claim 20 wherein the protein is a therapeutic, prophylactic or diagnostic agent.

28. The method of claim 20 wherein the solute concentration in said mixture is at least 0.1 weight/volume %.

29. The method of claim 20 wherein the solvent includes an alcohol.

30. The method of claim 20 wherein the spray-dried particles have a tap density less than about 0.4 g/cm$^3$.

31. The method of claim 20 wherein the spray-dried particles have a tap density less than about 0.1 g/cm$^3$.

32. The method of claim 20 wherein the spray-dried particles have a tap density less than about 0.05 g/cm$^3$.

33. The method of claim 20 wherein the spray-dried particles have a median geometric diameter of between about 5 microns and about 30 microns.

34. The method of claim 20 wherein the spray-dried particles have an aerodynamic diameter of between about 1 micron and about 5 micron.

35. The particles produced by the method of claim 20.

36. A method comprising administering to the respiratory tract of a patient in need of treatment, prophylaxis or diagnosis an effective amount of the spray-dried particles produced by the method of claim 20.

37. A method for producing spray-dried particles having improved stability of a protein comprising:
(a) combining a protein, a phospholipid, a buffer salt and a co-solvent, said co-solvent including an aqueous solvent and an organic solvent, to form a mixture; and
(b) spray-drying said mixture to produce spray-dried particles comprising a stabilized protein;
wherein the particles consist of the stabilized protein, the phospholipid and the buffer salt and wherein the phospholipid is present in the particles in an amount of at least about 10 weight percent.

38. A method for producing spray-dried particles having improved stability of a peptide comprising:
(a) combining a peptide, a phospholipid, a buffer salt and a co-solvent, said co-solvent including an aqueous solvent and an organic solvent, to form a mixture; and
(b) spray-drying said mixture to produce spray-dried particles comprising a stabilized peptide;
wherein the particles consist of the stabilized peptide, the phospholipid and the buffer salt and wherein the phospholipid is present in the particles in an amount of at least about 10 weight percent.

39. A method for producing spray-dried particles having improved stability of a protein comprising:
(a) combining a protein, a phospholipid, a buffer salt and an organic solvent, to form a mixture; and
(b) spray-drying said mixture to produce spray-dried particles comprising a stabilized protein;
wherein the particles consist of the stabilized protein, the phospholipid and the buffer salt and wherein the phospholipid is present in the particles in an amount of at least about 10 weight percent.

40. A method for producing spray-dried particles having improved stability of a peptide comprising:
(a) combining a peptide, a phospholipid, a buffer salt and an organic solvent, to form a mixture; and
(b) spray-drying said mixture to produce spray-dried particles comprising a stabilized peptide;
wherein the particles consist of the stabilized peptide, the phospholipid and the buffer salt and wherein the phospholipid is present in the particles in an amount of at least about 10 weight percent.

* * * * *